(12) United States Patent
Suita et al.

(10) Patent No.: US 9,283,306 B2
(45) Date of Patent: Mar. 15, 2016

(54) PHOTOACOUSTIC MATCHING MATERIAL AND HUMAN TISSUE SIMULATION MATERIAL

(71) Applicant: CANON KABUSHIKI KAISHA, Tokyo (JP)

(72) Inventors: Takahiro Suita, Kyoto (JP); Takuji Oishi, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/485,570

(22) Filed: Sep. 12, 2014

(65) Prior Publication Data

US 2014/0378573 A1 Dec. 25, 2014

Related U.S. Application Data

(62) Division of application No. 13/582,380, filed as application No. PCT/JP2011/054671 on Feb. 23, 2011, now abandoned.

(30) Foreign Application Priority Data

Mar. 9, 2010 (JP) .................... 2010-052418
Jan. 19, 2011 (JP) .................... 2011-009214

(51) Int. Cl.
| | |
|---|---|
| C08K 3/04 | (2006.01) |
| C08K 3/22 | (2006.01) |
| C08G 18/10 | (2006.01) |
| A61L 31/12 | (2006.01) |
| C08K 3/00 | (2006.01) |
| G09B 23/30 | (2006.01) |
| C08G 18/48 | (2006.01) |
| C08G 18/73 | (2006.01) |
| A61B 5/00 | (2006.01) |

(52) U.S. Cl.
CPC ............ *A61L 31/128* (2013.01); *A61B 5/0095* (2013.01); *C08G 18/4837* (2013.01); *C08G 18/73* (2013.01); *C08K 3/0033* (2013.01); *C08K 3/04* (2013.01); *C08K 3/22* (2013.01); *G09B 23/30* (2013.01); *C08K 2003/2241* (2013.01)

(58) Field of Classification Search
USPC ............... 523/105; 524/431, 495; 528/66
See application file for complete search history.

(56) References Cited

U.S. PATENT DOCUMENTS 4,356,516 A * 10/1982 Koguchi ............ H04N 1/36
358/426.12
2009/0286216 A1* 11/2009 Shikinami ............ A61B 8/00
434/262

FOREIGN PATENT DOCUMENTS

| JP | H09-145683 A | 6/1997 |
|---|---|---|
| JP | H10-330451 A | 12/1998 |
| JP | 2003-310610 A | 11/2003 |
| JP | 2007-189342 A | 7/2007 |
| JP | 2008-073341 A | 4/2008 |

* cited by examiner

*Primary Examiner* — Tae H Yoon
(74) *Attorney, Agent, or Firm* — Canon U.S.A. Inc., IP Division

(57) ABSTRACT

Since a medium having light propagation properties and sound propagation properties similar to those of human tissues is provided, reflection of light and an acoustic wave at a surface of a test portion is prevented, and accuracy control of a photoacoustic wave diagnostic apparatus is realized. A photoacoustic matching material is provided which includes a polyol, an inorganic oxide, and a pigment, the latter two being dispersable in the polyol, and in this photoacoustic matching material, a dispersed amount of the inorganic oxide to the polyol is in a range of 0.10 to 0.25 percent by weight, and a dispersed amount of the pigment to the polyol is in a range of 0.0001 to 0.0005 percent by weight.

4 Claims, 4 Drawing Sheets

PHOTOACOUSTIC MATCHING MATERIAL AND HUMAN TISSUE SIMULATION MATERIAL

CROSS REFERENCE TO RELATED APPLICATIONS

This application is a Divisional of U.S. patent application Ser. No. 13/582,380 filed Aug. 31, 2012, now abandoned which is a National Stage Entry of PCT/JP2011/054671 filed Feb. 23, 2011, and which claims priority to Japanese Patent Application No. 2011-009214 filed Jan. 19, 2011 and Japanese Patent Application No. 2010-052418 filed Mar. 9, 2010, all of which are hereby incorporated by reference herein in their entireties.

TECHNICAL FIELD

The present invention relates to a photoacoustic matching material and a human tissue simulation material, and more particularly relates to a photoacoustic matching material and a human tissue simulation material, each of which has optical properties and acoustic properties similar to those of human tissues.

BACKGROUND ART

A photoacoustic wave diagnostic apparatus is an apparatus in which, when a living body which is a test portion to be tested is irradiated with light, an image is displayed based on a detection signal of an acoustic wave (typically an ultrasonic wave) generated by thermal expansion of a measuring object. By this diagnostic apparatus, a specific material in the test portion, such as glucose or hemoglobin contained in blood or the like, is tested.

In the photoacoustic wave diagnostic apparatus, a probe is used to receive an acoustic wave. When an air layer is present between the probe and a living body and/or when the acoustic impedance of the probe is significantly different from that of a living body, an acoustic wave is reflected at the interface therebetween. For this reason, it is necessary to provide an acoustic matching material having acoustic properties similar to those of human tissues between the probe and a living body. In PTL 1, an acoustic matching material used for an acoustic wave probe and a manufacturing method thereof have been disclosed, the acoustic matching material having acoustic properties similar to those of human tissues and being formed from a base material of an elastomer or a resin and a composite powder having a higher acoustic impedance than that of the base material.

In addition, in a medical diagnostic apparatus, for the purposes of accuracy control and training of engineers, a human tissue model called a human tissue simulation material (hereinafter, referred to as a "phantom" in some cases) has been used. As a material for the phantom, a material which has properties similar to those of human tissues and which can be stored for a long period of time without causing, for example, the growth of bacteria has been desired.

In addition, PTL 2 has disclosed a non-corrosive acoustic wave phantom which has acoustic properties similar to those of human tissues and which is obtained by dispersing a powdered organic filler in a urethane resin functioning as a base material.

CITATION LIST

Patent Literature

PTL 1 Japanese Patent Laid-Open No. 2009-71393
PTL 2 Japanese Patent Laid-Open No. 2003-310610

SUMMARY OF INVENTION

Since the optical properties of the acoustic matching material disclosed in PTL 1 and those of the phantom disclosed in PTL 2 are different from the optical properties of human tissues, when the above materials are each used for a photoacoustic wave diagnostic apparatus, an acoustic wave is generated by scattering and/or absorption of light at an interface with a human body which is a subject to be tested. As a result, clear imaging in the vicinity of the interface may not be easily performed.

Although a material having light scattering properties is also included in the composite powder disclosed in PTL 1, since the volume fraction thereof is in a range of 50 to 70 percent by weight, the light scattering properties thereof are significant as compared to the optical properties of human tissues, and hence the optical properties of the composite powder may not be easily made similar to those of human tissues. In addition, in the case of the phantom disclosed in PTL 2 in which the powdered organic filler is used, the acoustic properties thereof may also be made similar to those of human tissues. However, since light absorption properties and light scattering properties are hardly obtained by a dispersed amount of the powdered organic filler disclosed in PTL 2, the optical properties thereof may not be easily made similar to those of human tissues.

Hence, the present invention provides a matching material and/or a phantom having not only acoustic properties similar to those of human tissues but also optical properties similar thereto.

In order to solve the above problems, through intensive research carried out by the present inventors, a photoacoustic matching medium having not only acoustic properties similar to those of human tissues but also optical properties similar thereto was discovered. A photoacoustic matching medium of the present invention includes a polyol, an inorganic oxide, and a pigment, the latter two being dispersable in the polyol, and in the above photoacoustic matching medium, a dispersed amount of the inorganic oxide to the polyol is in a range of 0.10 to 0.25 percent by weight, and a dispersed amount of the pigment to the polyol is in a range of 0.0001 to 0.0005 percent by weight.

In addition, the photoacoustic matching medium of the present invention may be used as a photoacoustic matching material or a phantom in a photoacoustic wave diagnostic apparatus.

Since having light propagation properties and sound propagation properties, both of which are similar to those of human tissues, when the photoacoustic matching material and the phantom of the present invention are each used in a photoacoustic diagnostic apparatus, reflection of an acoustic wave at an interface of a test portion and generation of an acoustic wave by irradiation light are suppressed.

DESCRIPTION OF EMBODIMENTS

Figure 1:
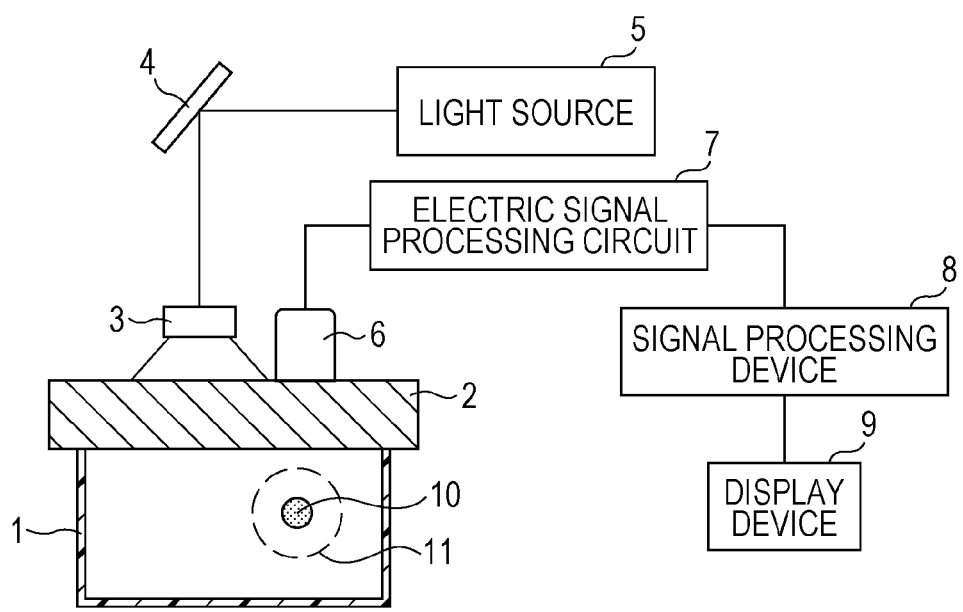
FIG. 1 is a schematic view of a photoacoustic wave diagnostic apparatus in which a photoacoustic matching material of the present invention which has light propagation properties and sound propagation properties similar to those of human tissues is placed at a test portion.

Hereinafter, embodiments of the present invention will be described with reference to the drawings and the like. The following embodiments are examples of a photoacoustic matching material and a human tissue simulation material (phantom) of the present invention; however, the present invention is not limited to the embodiments.

In addition, the importance of the present invention is a discovery of a matching material which is formed from a non-corrosive polyol used as a base material and which has acoustic properties and optical properties similar to those of a human body.

First Embodiment

A photoacoustic matching material according to a first embodiment of the present invention includes a polyol, an inorganic oxide, and a pigment, the latter two being dispersable in the polyol, and a dispersed amount of the inorganic oxide to the polyol is in a range of 0.1 to 0.25 percent by weight. In addition, a dispersed amount of the pigment to the polyol is in a range of 0.0001 to 0.0005 percent by weight. When the dispersed amounts are controlled as described above, a photoacoustic matching material having acoustic properties and optical properties similar to those of a human body can be obtained.

As a polyol used for the present invention, although a polyether polyol, a polyester polyol, a polycarbonate polyol, and the like may be mentioned, in terms of the similarity to the acoustic properties of a human body, a polyether polyol is more preferably used. In terms of the similarity to the sound propagation properties of a human body and the stability of a resin, the polyether polyol is preferably a copolymer which is formed from ethylene oxide and propylene oxide at a molar ratio in a range of 30:70 to 70:30 and which has a number average molecular weight in a range of approximately 6,000 to 8,000.

A polyol used for the photoacoustic matching material of the present invention is generally in a liquid state (including a gel state). If necessary, the polyol may be cured into a solid state by adding a curing agent. Although a curing agent used in this case is not particularly limited, in the present invention, an isocyanate compound is preferably used. As the isocyanate compound used in the present invention as a curing agent, a compound which can enable a polyol to have sound propagation properties similar to those of human tissues is preferable. As a particular example of the isocyanate compound described above, for example, hexamethylene diisocyanate (HDI), diphenylmethane diisocyanate (MDI), tolylene diisocyanate (TDI), isophorone diisocyanate (IPDI), or xylylene diisocyanate (XDI) may be mentioned.

In addition, when titanium oxide which is an inorganic oxide is dispersed in a polyol as a filler having light scattering properties, since the acoustic attenuation of the resin increases, a resin having a low acoustic attenuation is preferable. Since the acoustic attenuation of a resin prepared using HDI is very low, such as −0.12 dB/cm/MHz, HDI is particularly preferable. Although the case in which HDI is used will be described in this embodiment, in the present invention, other materials may also be used.

When the number average molecular weight of a photoacoustic matching material of the present invention containing a polyol and an isocyanate compound is high, the hardness is likely to decrease. In addition, when the number average molecular weight is low, the hardness is likely to increase. In terms of the similarity to the sound propagation properties of a human body, the number average molecular weight of the photoacoustic matching material of the present invention is preferably in a range of approximately 1,000 to 10,000.

As the filler having light scattering properties as described above, for example, an inorganic oxide, such as titanium oxide, may be mentioned. However, titanium oxide having no surface modification precipitates in a polyol and is not likely to be dispersed therein. For this reason, in order to uniformly disperse titanium oxide in a polyol, a coating film is preferably formed on the surface of titanium oxide. Although the case in which titanium oxide processed by a surface treatment using aluminum oxide and hexamethyldisilazane will be described in this embodiment, in the present invention, other materials may also be used. In addition, the dispersibility may be improved not only by forming a coating film but also by performing various surface modification techniques, such as methylation and ethylation, on the surface.

In the present invention, in view of light diffusion, the average particle diameter of the titanium oxide processed by a coating treatment on the surface thereof using aluminum oxide is preferably in a range of 0.2 to 0.3 μm. In this embodiment, although the case in which surface-treated titanium oxide having an average particle diameter of 0.21 μm is used will be described, in the present invention, titanium oxide having a different particle diameter may also be used.

As a filler having light absorption properties used for the present invention, a pigment is preferably used. As the pigment, for example, there may be mentioned a black pigment such as carbon black; a cyan pigment such as copper phthalocyanine; a magenta pigment, such as a monoazo lake pigment or a monoazo pigment; and a yellow pigment, such as diarylide yellow. However, since a pigment itself precipitates in a polyol and is not dispersed therein, a dispersion in which a pigment is covalently bonded to a polyol is preferably used. In the present invention, although a dispersion in which carbon black is covalently bonded to a polyether polyol is used, other polyols and pigments may also be used.

Hereinafter, a method for preparing a medium having light propagation properties and sound propagation properties similar to those of human tissues according to an embodiment of the present invention will be described. After a filler is dispersed in a polyol received in a beaker and is stirred, vacuum defoaming is performed. When resin curing is performed, after the vacuum defoaming is performed, an isocyanate compound functioning as a curing agent is added to the polyol, and subsequently, a mixture thus obtained is charged in a predetermined mold and is then heated at 90° C. for 1 hour.

Measurement results of the acoustic velocity and the acoustic attenuation are shown in Table 1 which are obtained when as a filler having light scattering properties, titanium oxide processed by a surface treatment using aluminum oxide and hexamethyldisilazane is dispersed in a resin including a polyol and an isocyanate compound. As the polyol, a copolymer (number average molecular weight: 7,000) of ethylene oxide and propylene oxide at a molar ratio of 50:50 was used. As the isocyanate compound, HDI was used. The addition amount of HDI was set to 3.4 percent by weight to the polyol. The average particle diameter of the titanium oxide processed by a surface treatment using aluminum oxide and hexamethyldisilazane was adjusted to 0.21 μm. In Table 1, the dispersed amount indicates a weight ratio of the titanium oxide to the polyol and is represented by percent by weight (wt %).

TABLE 1

| DISPERSED AMOUNT OF TiO$_2$ [wt %] | ACOUSTIC VELOCITY [m/s] | ACOUSTIC ATTENUATION [dB/cm/MHz] |
| --- | --- | --- |
| 0.00 | 1427.3 | 0.12 |
| 0.05 | 1420.5 | 0.22 |
| 0.10 | 1415.2 | 0.38 |
| 0.15 | 1402.8 | 0.46 |
| 0.20 | 1393.6 | 0.57 |
| 0.25 | 1383.5 | 0.68 |
| 0.50 | 1378.5 | 0.84 |
| 0.75 | 1362.4 | 1.08 |
| 1.00 | 1352.5 | 1.25 |

Since the acoustic velocity and the acoustic attenuation in a living fat tissue are in a range of 1,350 to 1,450 m/s and in a range of −0.20 to −1.3 dB/cm/MHz, respectively, the acoustic velocity and the acoustic attenuation of the photoacoustic matching material are also required within the above acoustic velocity range and acoustic attenuation range, respectively. The acoustic impedance defined by a product of the density of the photoacoustic matching material and the acoustic velocity therein is 1.5 MRayl. Since the density of the resin prepared in this embodiment is 1.13 regardless of the dispersed amount of titanium oxide, acoustic properties similar to those of a living body may be obtained by adjustment of the dispersed amount of titanium oxide. Hence, when the dispersed amount of the inorganic oxide to the polyol is set in a range of 0.1 to 1.0 percent by weight, a matching material having acoustic properties similar to those of a living body can be obtained. In addition, when the dispersed amount of titanium oxide was more than 1.0 percent by weight, a curing defect occurred, and hence a cured resin could not be obtained.

Next, in the case in which resin curing was not performed on a polyol (HDI was not added), and titanium oxide was dispersed in a liquid polyol, the acoustic velocity and the acoustic attenuation were measured, and the results thereof are shown in Table 2. As in the case in which the resin curing was performed, as the polyol, a copolymer (number average molecular weight: 7,000) of ethylene oxide and propylene oxide at a molar ratio of 50:50 was used. As the filler, titanium oxide (average particle diameter: 0.21 μm) processed by a surface treatment using aluminum oxide and hexamethyldisilazane was used. In the table, the dispersed amount indicates a weight ratio of the titanium oxide to the polyol and is represented by percent by weight.

TABLE 2

| DISPERSED AMOUNT OF TiO$_2$ [wt %] | ACOUSTIC VELOCITY [m/s] | ACOUSTIC ATTENUATION [dB/cm/MHz] |
| --- | --- | --- |
| 0.00 | 1475.5 | 0.09 |
| 0.05 | 1458.2 | 0.13 |
| 0.10 | 1449.4 | 0.26 |
| 0.15 | 1445.5 | 0.39 |
| 0.20 | 1442.2 | 0.51 |
| 0.25 | 1438.5 | 0.58 |
| 0.50 | 1431.2 | 0.78 |
| 0.75 | 1426.8 | 0.85 |
| 1.00 | 1421.2 | 0.95 |

From the results shown in Tables 1 and 2, it was found that, when no resin curing was performed, although the acoustic velocity was faster than that obtained when resin curing was performed, the acoustic properties were not significantly different from those of human tissues. From the above results, it was found that by adjustment of the particle diameter and the dispersed amount of titanium oxide with respect to the polyol, acoustic properties similar to those of a living body could be obtained. That is, even when the resin is not cured, if the dispersed amount of the inorganic oxide to the polyol is set in a range of 0.1 to 1.0 percent by weight, a matching material having acoustic properties similar to those of the living body (fat tissue) can be obtained.

Since the viscosity of the liquid polyol is approximately 700 mPa·s at 25° C. regardless of whether titanium oxide is dispersed or not, the polyol is in a gel state having liquidity at room temperature. In addition, since titanium oxide and the polyol are harmless to a human body, the polyol containing titanium oxide dispersed therein can be used as an acoustic matching material which is applied to a skin.

Next, as for an optical equivalent scattering coefficient μs', measurement results of a titanium oxide-dispersed polyol resin (HDI is added) and a titanium oxide-dispersed liquid polyol (no HDI is added) in each composition are shown in each of Tables 3 and 4. The measured wavelength in Table 3 was 756 nm which was the wavelength used as an index indicating the degree of oxygen saturation in blood. The measured wavelength in Table 4 was 1,064 nm. As the polyol, a copolymer (number average molecular weight: 7,000) of ethylene oxide and propylene oxide at a molar ratio of 50:50 was used. As the isocyanate compound for the resin curing, HDI was used. The addition amount of HDI was set to 3.4 percent by weight to the polyol. As the filler, titanium oxide (average particle diameter: 0.21 μm) processed by a surface treatment using aluminum oxide and hexamethyldisilazane was used. In the table, the dispersed amount indicates a weight ratio of the titanium oxide to the polyol.

TABLE 3

| DISPERSED AMOUNT OF TiO$_2$ [wt %] | EQUIVALENT SCATTERING COEFFICIENT (LIQUID) [mm$^{-1}$] | EQUIVALENT SCATTERING COEFFICIENT (RESIN) [mm$^{-1}$] |
| --- | --- | --- |
| 0.00 | 0.06 | 0.04 |
| 0.05 | 0.48 | 0.47 |
| 0.10 | 0.56 | 0.58 |
| 0.15 | 0.62 | 0.64 |
| 0.20 | 0.70 | 0.72 |
| 0.25 | 0.78 | 0.76 |
| 0.50 | 1.28 | 1.25 |
| 0.75 | 1.37 | 1.38 |
| 1.00 | 1.54 | 1.51 |

TABLE 4

| DISPERSED AMOUNT OF $TiO_2$ [wt %] | EQUIVALENT SCATTERING COEFFICIENT (LIQUID) [mm$^{-1}$] | EQUIVALENT SCATTERING COEFFICIENT (RESIN) [mm$^{-1}$] |
| --- | --- | --- |
| 0.00 | 0.03 | 0.02 |
| 0.05 | 0.38 | 0.40 |
| 0.10 | 0.45 | 0.46 |
| 0.15 | 0.52 | 0.54 |
| 0.20 | 0.59 | 0.61 |
| 0.25 | 0.65 | 0.68 |
| 0.50 | 1.15 | 1.18 |
| 0.75 | 1.26 | 1.31 |
| 1.00 | 1.45 | 1.48 |

The equivalent scattering coefficient in a living body decreases approximately monotonically with an increase in wavelength. As for the equivalent scattering coefficient in a living body, it has been known that the equivalent scattering coefficient μs' is 0.45 to 1.15 mm$^{-1}$ at a wavelength of 756 nm, and the equivalent scattering coefficient μs' is 0.4 to 0.95 mm$^{-1}$ at a wavelength of 1,064 nm. As apparent from Tables 3 and 4, when titanium dioxide is not dispersed in the polyol, the equivalent scattering coefficient is smaller than that of a living body, and hence the optical properties cannot be reproduced.

Therefore, the lower limit of the dispersed amount of titanium oxide to the polyol must be an amount which at least satisfies the lower limit or more of the equivalent scattering coefficient of a living body. That is, from Tables 3 and 4, it is found that in order to satisfy this condition, 0.1 percent by weight or more of titanium oxide is required.

As for the upper limit of the dispersed amount of titanium oxide to the polyol, when the dispersed amount of titanium oxide is 0.50 percent by weight, the equivalent scattering coefficient of a living body is not reproduced. Hence, in the present invention, the dispersed amount of an inorganic oxide to the polyol is set in a range of 0.1 to 0.25 percent by weight. By controlling the dispersed amount as described above, a matching material having optical properties similar to those of a living body can be obtained.

In addition, as apparent from the results shown in Tables 3 and 4, since the resin curing has substantially no influence on optical properties, even if resin curing is not performed, optical properties similar to those of a living body can be obtained.

Next, as for a light absorption coefficient μa, measurement results of a filler-dispersed polyol of each composition are shown in Tables 5 and 6. Table 5 shows the measurement results at a wavelength of 756 nm, and Table 6 shows the measurement results at a wavelength of 1,064 nm. As the polyol, a copolymer (number average molecular weight: 7,000) of ethylene oxide and propylene oxide at a molar ratio of 50:50 was used. As the isocyanate compound for resin curing, HDI was used. As the filler, titanium oxide processed by a surface treatment using aluminum oxide and a polyol-bonded black pigment (carbon black) dispersion were used. In the table, the dispersed amount indicates a weight ratio of the black pigment to the polyol. The dispersed amount of titanium oxide processed by a surface treatment was set to 0.2 percent by weight to the polyol. The addition amount of HDI was set to 3.4 percent by weight to the polyol.

TABLE 5

| DISPERSED AMOUNT OF BLACK PIGMENT [wt %] | ABSORPTION COEFFICIENT (LIQUID) [mm$^{-1}$] | ABSORPTION COEFFICIENT (RESIN) [mm$^{-1}$] |
| --- | --- | --- |
| 0.0000 | 0.0007 | 0.0008 |
| 0.0001 | 0.0045 | 0.0042 |

TABLE 5-continued

| DISPERSED AMOUNT OF BLACK PIGMENT [wt %] | ABSORPTION COEFFICIENT (LIQUID) [mm$^{-1}$] | ABSORPTION COEFFICIENT (RESIN) [mm$^{-1}$] |
| --- | --- | --- |
| 0.0002 | 0.0058 | 0.0055 |
| 0.0004 | 0.0070 | 0.0068 |
| 0.0005 | 0.0078 | 0.0082 |
| 0.0010 | 0.0126 | 0.0128 |

TABLE 6

| DISPERSED AMOUNT OF BLACK PIGMENT [wt %] | ABSORPTION COEFFICIENT (LIQUID) [mm$^{-1}$] | ABSORPTION COEFFICIENT (RESIN) [mm$^{-1}$] |
| --- | --- | --- |
| 0.0000 | 0.0010 | 0.0010 |
| 0.0001 | 0.0045 | 0.0052 |
| 0.0002 | 0.0062 | 0.0068 |
| 0.0004 | 0.0092 | 0.0094 |
| 0.0005 | 0.0107 | 0.0119 |
| 0.0010 | 0.0140 | 0.0142 |

As for the light absorption coefficient in a living body (fat tissue), the absorption coefficients μa are 0.002 to 0.009 mm$^{-1}$ and 0.004 to 0.015 mm$^{-1}$ at wavelengths of 756 nm and 1,064 nm, respectively. As apparent from Tables 5 and 6, when no black pigment is dispersed in the polyol, since the absorption coefficient is smaller than that of a living body, the optical properties of a living body cannot be reproduced. Therefore, the optimal range of the dispersed amount of the black pigment to the polyol is estimated as follows.

The lower limit of the dispersed amount of the black pigment to the polyol must be an amount which at least satisfies the lower limit or more of the absorption coefficient of a living body. That is, from Tables 5 and 6, it is found that in order to satisfy this condition, 0.0001 percent by weight or more of the black pigment is required.

On the other hand, as for the upper limit, since the absorption coefficient of a living body is not reproduced when the dispersed filler amount to the polyol is 0.0010 percent by weight, in the present invention, the dispersed amount of the black pigment to the polyol is preferably in a range of 0.0001 to 0.0005 percent by weight. From the results shown in Tables 5 and 6, since the resin curing has substantially no influence on optical properties, even if resin curing is not performed, optical properties similar to those of a living body can be obtained. In addition, by the dispersed amount of the black pigment within the ranges shown in Tables 5 and 6, the equivalent scattering coefficient and the acoustic properties were not substantially influenced.

From the above results, the optical properties of a living body can be simulated by adjustment of the dispersed amounts of titanium oxide and a pigment. Hence, according to the results shown in Tables 1 to 6, the photoacoustic matching material of the present invention includes a polyol, an inorganic oxide, and a pigment, the latter two being dispersable in the polyol, and the dispersed amount of the inorganic oxide to the polyol is in a range of 0.1 to 0.25 percent by weight. In addition, the dispersed amount of the pigment to the polyol is in a range of 0.0001 to 0.0005 percent by weight.

In addition, since acoustic properties and optical properties similar to those of a living body can be obtained, the photoacoustic matching material of the present invention is preferably prepared so that the acoustic velocity is in a range of 1,350 to 1,450 m/s, the acoustic attenuation is in a range of 0.20 to 1.3 dB/cm/MHz, and with respect to light having a wavelength in a range of 756 to 1,064 nm, the equivalent scattering coefficient and the absorption coefficient are in a range of 0.4 to 1.15 mm$^{-1}$ and in a range of 0.002 to 0.015 mm$^{-1}$, respectively.

As described above, a photoacoustic matching material having light propagation properties and sound propagation properties similar to those of human tissues can be prepared by adjustment of the dispersed amount of titanium oxide. In addition, since the water absorption rate of a polyol in which titanium oxide is dispersed is low regardless of whether the resin curing is performed or not, a non-corrosive photoacoustic matching material can be prepared. Since the viscosity of the liquid polyol is approximately 700 mPa·s at 25° C. regardless of whether titanium oxide is dispersed or not, the polyol is in a gel state having liquidity at room temperature. In addition, since the polyol and the filler of the present invention are harmless to a human body, the liquid polyol containing a filler dispersed therein can be used as a photoacoustic matching material which is applied to a skin.

When a liquid-containing bag or the like is used as a matching material to be in contact with a test portion, a bag or a container is formed, and a filler-dispersed liquid polyol is charged therein. In this case, the thickness of the bag or the container is preferably in a range of approximately 0.05 to 10 mm. Although a filler-dispersed cured polyol is preferably used as a material for the bag or the container, a material, such as poly(methyl pentene), having acoustic impedance similar to that of human tissues and transparency may also be used for a thin film. Since a sanitary aspect is also taken into consideration, at least a part which is to be in contact with a test portion is preferably configured to be changeable for every subject.

Evaluation Method of Acoustic Properties

Hereinafter, an evaluation method of acoustic properties of the present invention will be described. As an ultrasonic transducer (transmission section) functioning as a probe used for acoustic property evaluation, V303 manufactured by Olympus NDT (center frequency: 1 MHz) was used. As a hydrophone (receive section), a needle type hydrophone PAL-1384 manufactured by Precision Acoustics was used. The transducer and the hydrophone were fixed in a water tank with a jig so that the centers of sound axes thereof coincided with each other. The distance between the transducer and the hydrophone was set to 40 mm.

When a cured polyol was measured, a cured polyol (such as a gel sheet of a urethane resin) adjusted to have a size of 100 mm by 100 mm and a thickness of 5 or 10 mm was fixed between the above experimental transducer and hydrophone with a jig so that an incident angle of a photoacoustic wave with respect to the gel sheet was 0°. A sine wave (transmission voltage: 50V) of one cycle was transmitted from the transducer using a function generator (AFG3022 manufactured by Tectronix), and a received voltage value of the hydrophone in each sheet placement was obtained using an oscilloscope (TDS3012C manufactured by Tectronix). The acoustic velocity was obtained from the difference in arrival time of a received wave between gel sheet placement and no gel sheet placement using an oscilloscope. The acoustic attenuation was obtained from the following formula.

$$\text{ACOUSTIC ATTENUATION PER 1 cm/1 MHz (dB/cm/MHz)} = 20 \times \log\left\{\frac{\text{RECEIVED ACOUSTIC PRESSURE IN 10 mm-THICK SHEET PLACEMENT}}{\text{RECEIVED ACOUSTIC PRESSURE IN 5 mm-THICK SHEET PLACEMENT}}\right\} \times \frac{10 \text{ (mm)}}{5 \text{ (mm)}}$$

[Math. 1]

The acoustic properties of a non-cured liquid polyol was calculated in a manner similar to that for the cured polyol by charging a polyol in a polycarbonate cell (cell thickness: 1.5 mm) having a size of 100 mm by 100 mm and an inside width of 5 or 10 mm.

Evaluation Method of Optical Properties

Next, an evaluation method of optical properties of the present invention will be described. A liquid polyol was charged in a quartz cell having a size of 50 mm by 50 mm and an optical path length of 5 mm, or after being charged in the quartz cell, the polyol was cured by heating at 90° C. for 1 hour, so that a cell for measurement of optical properties was prepared. The transmittance and the reflectance were obtained using this cell by a spectrophotometer V-670 manufactured by JASCO Corp. In addition, the refractive index was obtained using a refractometer KPR-2000 manufactured by Shimadzu Corp. By Monte Carlo simulation, the variable setting was optimized using the results thus obtained so that the difference between the measured value and the calculated value is minimized, and the equivalent scattering coefficient and the absorption coefficient at each wavelength were calculated.

Second Embodiment

Next, an example of use of the photoacoustic matching material of the present invention will be described. The form of the photoacoustic matching material may be either a liquid (including a gel at room temperature (approximately 25° C.)) or a solid and is not particularly limited. That is, a liquid photoacoustic matching material containing no isocyanate compound or a solid photoacoustic matching material containing an isocyanate compound is obtained. In addition, the photoacoustic matching material is primarily used in order to fill a space between a test portion and a probe or a probe unit of a photoacoustic wave diagnostic apparatus. As particular examples, Example 1 (FIG. 1) and Example 2 (FIG. 2) will be described.

In order to cover a test portion having a unique shape without forming any spaces therebetween, a liquid photoacoustic matching material is preferably used. In this case, a container which houses the above liquid is also preferably formed of a solid photoacoustic matching material of the present invention. That is, the liquid photoacoustic matching material containing no isocyanate compound is preferably housed in the solid photoacoustic matching material containing an isocyanate compound. The "house" in this case may indicate both cases in which the liquid photoacoustic matching material is housed in the solid photoacoustic matching material in an air-tight state and in non-air-tight state.

Figure 3A:
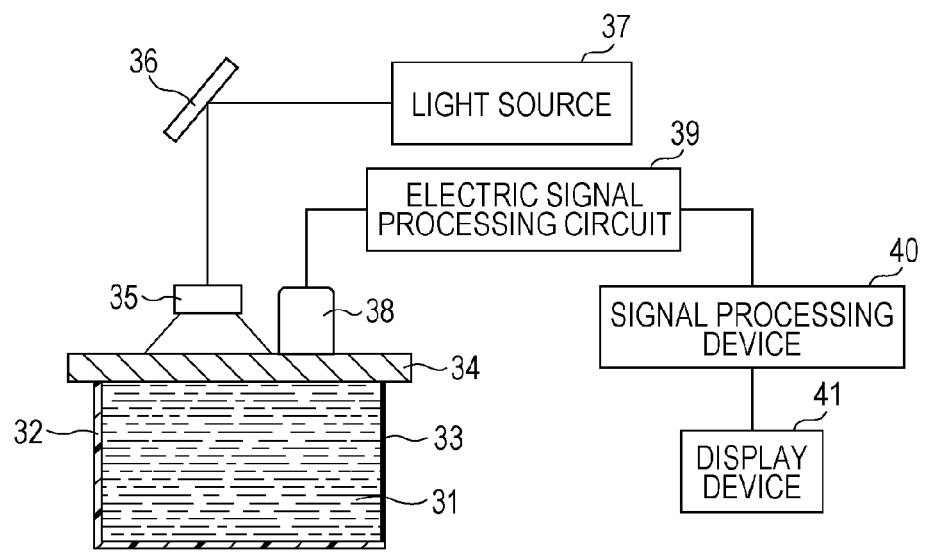
FIG. 3A is a schematic view showing the case in which a container formed from a photoacoustic matching material of the present invention is applied to a photoacoustic wave diagnostic apparatus.
Figure 3B:
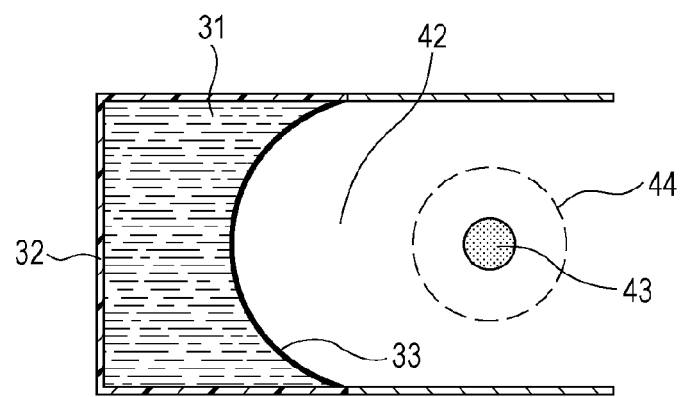
FIG. 3B is a schematic view showing the case in which a test portion is placed in the container formed from the photoacoustic matching material of the present invention.

For example, when a liquid-containing bag or the like is used as a matching material to be in contact with a test portion, a bag or a container is formed from a thin film, and a liquid titanium oxide-dispersed polyol is charged therein. In this case, the thickness of the thin film is preferably in a range of approximately 0.05 to 5 mm. Although a material for the thin film is not particularly limited as long as it has acoustic impedance similar to that of human tissues, transparency, and stretchable properties, in the present invention, a solid titanium oxide-dispersed polyol is preferably used. A particular example will be described in Example 3 (FIGS. 3A and 3B).

Since a sanitary aspect is also taken into consideration, at least a part which is to be in contact with a test portion is preferably configured to be changeable for every subject.

Third Embodiment

Figure 4:
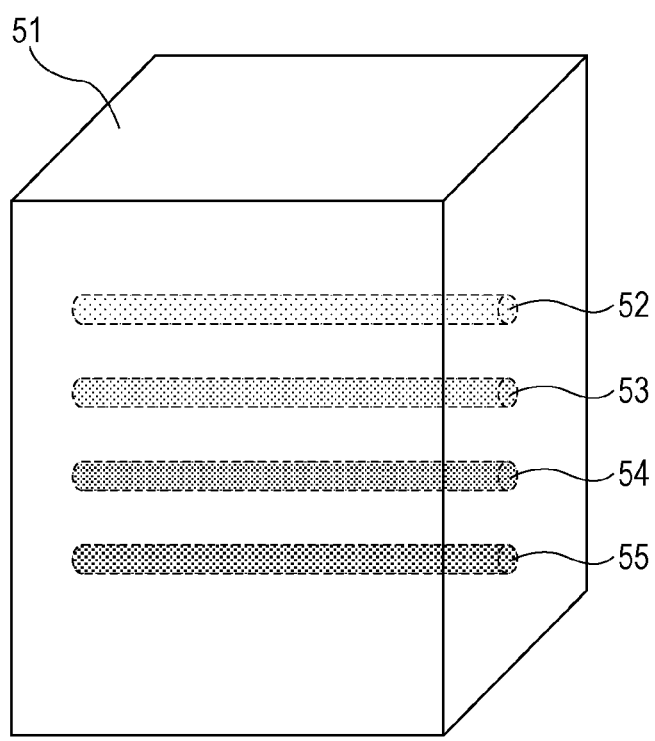
FIG. 4 is a schematic view showing the case in which a photoacoustic matching material of the present invention is used as a phantom for a photoacoustic wave diagnostic apparatus.

A third embodiment of the present invention is a phantom for a photoacoustic wave diagnostic apparatus which is a human tissue simulation material for a photoacoustic wave diagnostic apparatus containing at least one photoacoustic matching material of the present invention. The phantom for a photoacoustic wave diagnostic apparatus includes a cyst material (object for detection which simulates a blood vessel or the like) and a base material. In this embodiment, the cyst material and the base material are formed from the same material, and the photoacoustic matching material of the present invention is preferably used therefor; however, the cyst material and the base material may be formed from different materials. According to this embodiment, as a cyst material, a material in which a predetermined amount of a black pigment is dispersed in the photoacoustic matching material of the present invention is used, and the absorption coefficient μa thereof is calculated. A particular example will be described in Example 4 (FIG. 4).

As a particular example of a method for manufacturing a photoacoustic matching material of the present invention, for example, there may be mentioned a method in which after titanium oxide is dispersed in a polyol received in a beaker and stirred, vacuum defoaming is performed. In addition, in phantom manufacturing, when a cyst material which is an object for detection used as a simulated blood vessel is prepared, a black pigment is further dispersed. When resin curing is performed, for example, a method may be mentioned in which after vacuum defoaming is performed, an isocyanate compound used as a curing agent is added to the above dispersion, and a mixture thus obtained is charged in a predetermined mold and heated at 90° C. for 1 hour.

EXAMPLES

Hereinafter, although the features of the present invention will be described in more detail with reference to the following examples, the present invention is not limited to these examples, and as long as a photoacoustic matching material has functions and advantages similar to those described above, materials, composition conditions, reaction conditions, and the like may be freely changed.

Example 1

FIG. 1 is a schematic view showing the case in which the photoacoustic matching material of the present invention is used for a photoacoustic wave diagnostic apparatus. The photoacoustic wave diagnostic apparatus shown in FIG. 1 at least includes a test portion 1, a probe 6 which has an acoustic wave receiving function, a light source 5, a mirror 4, a light irradiation portion 3, an electric signal processing circuit 7, a signal processing device 8, and a display device 9. A photoacoustic matching material 2 is used in contact with the test portion 1 and the probe 6.

In the photoacoustic wave diagnostic apparatus, the test portion 1 is irradiated with light by the light irradiation portion 3 through the photoacoustic matching material 2. When a region (cyst material) 10 having high optical absorption properties is present in the test portion 1, an acoustic wave 11 (photoacoustic wave) resulting from thermal expansion by photoirradiation is generated. The probe 6 detects this acoustic wave 11 and converts it into an electric signal (analog signal). In addition, for example, A/D conversion of the electric signal is performed by the electric signal processing circuit 7, and image reconstruction (generation of image data) is performed by the signal processing device 8. In addition, the image data is displayed using the display device 9.

The photoacoustic matching material 2 of this example was formed such that 0.2 percent by weight of titanium oxide which was covered with a film of aluminum oxide and which had a particle diameter of 0.21 μm and 0.0005 percent by weight of a polyol-bonded black pigment (carbon black) dispersion to a polyol were dispersed therein. In addition, 3.4 percent by weight of HDI was added to the polyol, so that the preparation was performed. As the polyol, a copolymer (number average molecular weight: 7,000) of ethylene oxide and propylene oxide at a molar ratio of 50:50 was used. As the photoacoustic properties of the photoacoustic matching material in this example, the acoustic velocity was 1393.6 m/s and the acoustic attenuation was 0.57 dB/cm/MHz. In addition, at a wavelength of 756 nm, the equivalence scattering coefficient μs' and the absorption coefficient μa were 0.72 $mm^{-1}$ and 0.0082 $mm^{-1}$, respectively, and at a wavelength of 1,064 nm, the equivalence scattering coefficient μs' and the absorption coefficient μa were 0.61 $mm^{-1}$ and 0.0119 $mm^{-1}$, respectively. Therefore, a photoacoustic matching material having photoacoustic properties approximately equal to those of human tissues was obtained in this example.

When the photoacoustic matching material 2 is brought into contact with the probe and a living body, the acoustic attenuation caused by an air layer can be prevented. In addition, since the photoacoustic matching material 2 has light propagation properties and sound propagation properties, which are similar to those of a living body, reflection at the interface can be prevented.

Furthermore, if a filler-dispersed liquid polyol which is not cured is applied to the surface of a living body, the generation of an air layer caused by wrinkles of a skin can be prevented when the probe is pressure-contacted therewith.

Example 2

Figure 2:
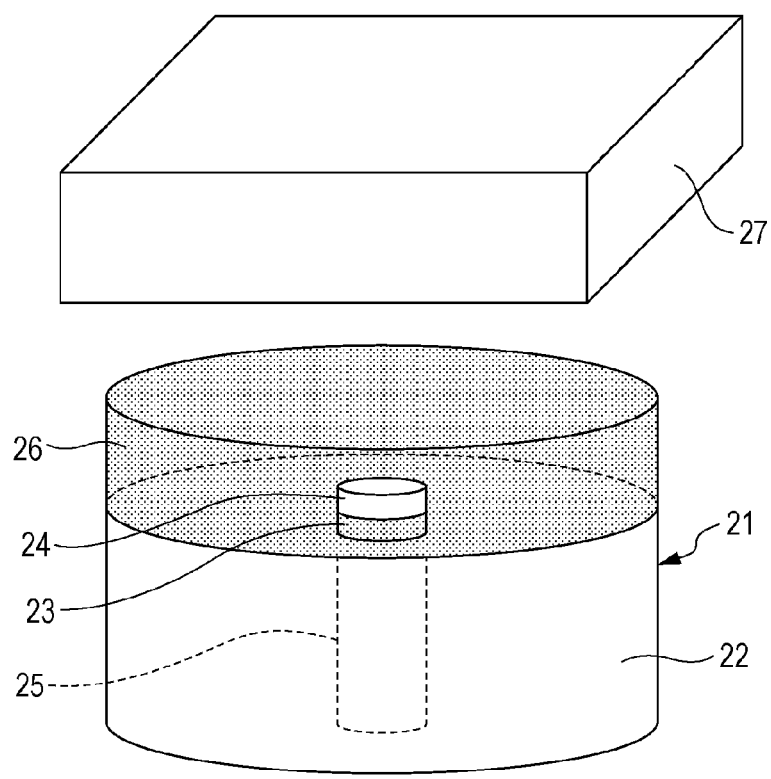
FIG. 2 is a schematic view showing a probe unit in which in the present invention, a light irradiation portion and an acoustic wave probe are integrated with each other.

An example in which the photoacoustic matching material of the present invention is bonded to a light irradiation portion and a probe of a photoacoustic wave diagnostic apparatus will be described with reference to FIG. 2. In FIG. 2, reference numeral 21 indicates a probe unit in which a light irradiation portion and an acoustic wave probe of a photoacoustic wave diagnostic apparatus are integrated with each other. The probe unit 21 includes a light guide tube 22, an acoustic wave probe 23, an acoustic matching layer 24, and a signal transmission portion 25, and a photoacoustic matching material 26 of the present invention is provided at a front end of the probe unit 21. As the photoacoustic matching material 26, a liquid-containing bag was used which included a bag formed of a thin film having a thickness of 0.05 mm and photoacoustic matching properties and a polyol enclosed in the bag, and in addition, with respect to the polyol, 0.2 percent by weight of titanium oxide coated with a film of aluminum oxide and 0.0005 percent by weight of a polyol-bonded black pigment dispersion were dispersed in the polyol. As the polyol, a copolymer (number average molecular weight: 7,000) of ethylene oxide and propylene oxide at a molar ratio of 50:50 was used. In addition, the probe unit 21 was used in the state in which the photoacoustic matching material 26 was in close contact with a subject 27.

Light passing through the light guide tube 22 is radiated toward the subject 27 and is absorbed by a light absorber, such as a blood vessel, present inside the subject, and an acoustic wave is generated by light excitation. This acoustic wave transmits the subject 27, the photoacoustic matching material 26, and the acoustic wave matching layer 24 and is changed into an electric signal by the acoustic wave probe 23, and this signal can be obtained through the signal transmission portion 25. When the photoacoustic matching material 26 of the present invention is not provided, and light enters the subject 27 directly from the light guide tube 22, an acoustic wave is generated at the interface of the subject 27. Since being superimposed on an acoustic wave generated from the light absorber present inside the subject, more particularly, in a region in the vicinity of the interface of the subject, the above acoustic wave functions as an undesirable noise for the acoustic wave generated from the light absorber. As described above, when the acoustic wave is generated at the interface of the subject, observation in the vicinity of the interface inside the subject cannot be easily carried out.

By providing the photoacoustic matching material 26 of the present invention at the front end of the probe unit 21, the above problem can be avoided, and furthermore, the acoustic wave can be propagated without causing any problems. As the photoacoustic matching material 26, a liquid-containing bag was used which included a bag formed of a stretchable thin film obtained from a cured filler-dispersed polyol and a filler-dispersed polyol enclosed in the bag. As the photoacoustic properties of the cured filler-dispersed thin film, the acoustic velocity was 1393.6 m/s, and the acoustic attenuation was 0.57 dB/cm/MHz. In addition, at a wavelength of 756 nm, the equivalence scattering coefficient $\mu s'$ and the absorption coefficient $\mu a$ were 0.72 mm$^{-1}$ and 0.0082 mm$^{-1}$, respectively, and at a wavelength of 1,064 nm, the equivalence scattering coefficient $\mu s'$ and the absorption coefficient $\mu a$ were 0.61 mm$^{-1}$ and 0.0119 mm$^{-1}$, respectively. In addition, as the photoacoustic properties of the filler-dispersed liquid polyol, the acoustic velocity was 1442.2 m/s, and the acoustic attenuation was 0.51 dB/cm/MHz. In addition, at a wavelength of 756 nm, the equivalence scattering coefficient $\mu s'$ and the absorption coefficient $\mu a$ were 0.70 mm$^{-1}$ and 0.0078 mm$^{-1}$, respectively, and at a wavelength of 1,064 nm, the equivalence scattering coefficient $\mu s'$ and the absorption coefficient $\mu a$ were 0.59 mm$^{-1}$ and 0.0107 mm$^{-1}$, respectively. Although the light radiated from the light guide tube 22 enters the photoacoustic matching material 26, in this case, an acoustic wave is generated at the interface between the photoacoustic matching material 26 and the light guide tube 22. Although light further travels toward the subject 27, since the optical properties of the subject 27 are similar to those of the photoacoustic matching material 26, the generation of the acoustic wave at the interface therebetween is suppressed. Furthermore, since the acoustic properties of the photoacoustic matching material 26 are similar to those of the subject 27, the acoustic wave generated from the light absorber inside the subject is propagated to the photoacoustic matching material 26 without being reflected and is changed into an electric signal by the acoustic wave probe 23 through the acoustic matching layer 24, so that the signal can be obtained through the signal transmission portion 25.

By providing the photoacoustic matching material 26 at the front end of the probe unit 21, the noise generated at the interface was suppressed to a level of approximately one hundredth and could be ignored. As described above, by bonding the photoacoustic matching material having light propagation properties and sound propagation properties similar to those of human tissues to the probe unit, the acoustic wave generated from the light absorber inside the subject is clearly obtained, and the quality of imaging inside the subject can be improved.

In this example, as the photoacoustic matching material 26, although the liquid-containing bag was used which included a bag formed of a thin film having acoustic matching properties and a filler-dispersed polyol enclosed in the bag, the polyol containing titanium oxide and carbon black dispersed therein, when a cured filler-dispersed polyol similar to that of Example 1 was used, an effect similar to that described above can also be obtained. Furthermore, if a filler-dispersed polyol which is not cured is applied to the liquid-containing bag, the generation of an air layer caused by wrinkles of the liquid-containing bag can be prevented when the probe is pressure-contacted therewith.

Example 3

An example in which a container formed of the photoacoustic matching material of the present invention is applied to a photoacoustic wave diagnostic apparatus will be described with reference to FIGS. 3A and 3B. A photoacoustic wave diagnostic apparatus shown in FIG. 3A includes an automatically scannable probe 38 having an acoustic wave receiving function, a support plate 34 of a subject used in contact therewith, a light source 37, a mirror 36, a light irradiation portion 35 which irradiates a test portion with light, an electric signal processing circuit 39, a signal processing device 40, and a display device 41. In this example, a container 32 is used which contains a liquid photoacoustic matching material 31 therein and which has a wall surface formed of a resin-cured photoacoustic matching material. In the photoacoustic wave diagnostic apparatus shown in FIG. 3A, FIG. 3B shows a cross-sectional view of the container 32 when a test portion 42 is placed therein.

The acoustic wave diagnostic apparatus performs photoirradiation to the test portion 42 by the light irradiation portion 35 through the support plate 34 and the container 32. When a region 43 having high optical absorption properties is present in the test portion 42, an acoustic wave 44 resulting from thermal expansion by photoirradiation is generated. The probe 38 detects this acoustic wave, and a screen display is performed using the electric signal processing circuit 39, the signal processing device 40, and the display device 41.

The container 32 of this example was prepared such that 0.2 percent by weight of titanium oxide having a particle diameter of 0.21 μm and coated with a film of aluminum oxide and 0.0005 percent by weight of a polyol-bonded black pigment (carbon black) dispersion to a polyol were dispersed therein, and 3.4 percent by weight of HDI was added to the polyol. As the polyol, a copolymer (number average molecular weight: 7,000) of ethylene oxide and propylene oxide at a molar ratio of 50:50 was used. The wall thickness of the container 32 was set to 5 mm. In addition, in this example, a surface of the container 32 which was in contact with the test portion was at least formed of a stretchable thin film 33. In this example, for the thin film 33, a cured filler-dispersed polyol similar to that for the container 32 was used. The thickness of the thin film 33 in this example was set to 50 μm.

As the photoacoustic properties of the photoacoustic matching material used for the container 32 and the thin film 33 of this example, the acoustic velocity was 1393.6 m/s, and the acoustic attenuation was 0.57 dB/cm/MHz. In addition, at a wavelength of 756 nm, the equivalence scattering coefficient $\mu s'$ and the absorption coefficient $\mu a$ were 0.72 mm$^{-1}$ and 0.0082 mm$^{-1}$, respectively, and at a wavelength of 1,064 nm, the equivalence scattering coefficient $\mu s'$ and the absorption coefficient $\mu a$ were 0.61 mm$^{-1}$ and 0.0119 mm$^{-1}$, respectively. In addition, for the liquid photoacoustic matching material 31 charged in the container 32 formed of the photoacoustic matching material, a polyol was used in which to the polymer, 0.2 percent by weight of titanium oxide coated with aluminum oxide and 0.0005 percent by weight of a polyol-bonded black pigment (carbon black) dispersion were dispersed. As the polyol, a copolymer (number average molecular weight: 7,000) of ethylene oxide and propylene oxide at a molar ratio of 50:50 was used. As the photoacoustic properties of the liquid photoacoustic matching material of this example, the acoustic velocity was 1442.2 m/s, and the acoustic attenuation was 0.51 dB/cm/MHz. In addition, at a wavelength of 756 nm, the equivalence scattering coefficient $\mu s'$ and the absorption coefficient $\mu a$ were 0.70 mm$^{-1}$ and 0.0078 mm$^{-1}$, respectively, and at a wavelength of 1,064 nm, the equivalence scattering coefficient $\mu s'$ and the absorption coefficient $\mu a$ were 0.59 mm$^{-1}$ and 0.0107 mm$^{-1}$, respectively.

Therefore, in this example, a photoacoustic matching material having photoacoustic properties approximately equal to those of human tissues was obtained.

By inserting a subject into the container 32, the noise generated at the interface was suppressed to a level of approximately one hundredth and could be ignored. As described above, since the container formed of the photoacoustic matching material having light propagation properties and sound propagation properties similar to those of human tissues is brought into contact with a test portion, the acoustic wave generated from the light absorber inside the subject is clearly obtained, and the quality of imaging inside the subject can be improved.

Example 4

An example in which the photoacoustic matching material of the present invention is applied to a phantom for a photoacoustic wave diagnostic apparatus will be described with reference to FIG. 4. In a phantom for a photoacoustic wave diagnostic apparatus shown in FIG. 4, cyst materials (1) to (4) designated by reference numerals 52 to 55 which were objects for detection used as simulated blood vessels were arranged in a base material 51 formed of a photoacoustic matching material having light propagation properties and sound propagation properties similar to those of human tissues. The size of the phantom was set to 120×70×50 mm. The base material 51 of the phantom for a photoacoustic wave diagnostic apparatus of the present invention was prepared such that 0.2 percent by weight of titanium oxide coated with a film of aluminum oxide and 0.0005 percent by weight of a polyol-bonded black pigment (carbon black) dispersion to a polyol were dispersed therein, and 3.4 percent by weight of HDI was added to the polyol. As the polyol, a copolymer (number average molecular weight: 7,000) of ethylene oxide and propylene oxide at a molar ratio of 50:50 was used. As the photoacoustic properties of the base material of this example, the acoustic velocity was 1393.6 m/s, and the acoustic attenuation was 0.57 dB/cm/MHz. In addition, at a wavelength of 756 nm, the equivalence scattering coefficient $\mu s'$ and the absorption coefficient $\mu a$ were 0.72 mm$^{-1}$ and 0.0082 mm$^{-1}$, respectively, and at a wavelength of 1,064 nm, the equivalence scattering coefficient $\mu s'$ and the absorption coefficient $\mu a$ were 0.61 mm$^{-1}$ and 0.0119 mm$^{-1}$, respectively. Therefore, in this example, a base material having photoacoustic properties approximately equal to those of human tissues was obtained.

The cyst materials (1) to (4) were prepared by dispersing a black pigment (carbon black) in the same material as that for the base material. In this case, the contrast of a detection image using a photoacoustic wave diagnostic apparatus was evaluated by calculating the absorption coefficient $\mu a$ to the dispersed amount of the black pigment. In addition, accuracy evaluation of a photoacoustic wave diagnostic apparatus was performed by arranging the cyst materials inside the phantom. In this example, cylindrical cyst materials each adjusted to have a diameter of 2 mm and a length of 70 mm were arranged inside the phantom. In Table 7, the absorption coefficients $\mu a$ of the base material and the cyst materials at a measurement wavelength of 1,064 nm and the contrast ratio of the cyst material to the base material are shown. Since the absorption coefficient $\mu a$ of blood is approximately 0.05 mm$^{-1}$, the accuracy control for hemoglobin detection of a photoacoustic wave diagnostic apparatus can be performed by using the phantom for a photoacoustic wave diagnostic apparatus of this example. In addition, by using the phantom for a photoacoustic wave diagnostic apparatus of this example, the accuracy control of a contrast ratio in a range of 5 to 20 dB to the base material can be performed.

TABLE 7

|  | ABSORPTION COEFFICIENT [mm$^{-1}$] | CONTRAST [dB] |
|---|---|---|
| BASE MATERIAL | 0.0088 | — |
| CYST MATERIAL (1) | 0.0158 | 5.08 |
| CYST MATERIAL (2) | 0.0285 | 10.21 |
| CYST MATERIAL (3) | 0.0498 | 15.05 |
| CYST MATERIAL (4) | 0.0890 | 20.10 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-052418, filed Mar. 9, 2010, and No. 2011-009214, filed Jan. 19, 2011, which are hereby incorporated by reference herein in their entirety.

REFERENCE SIGNS LIST 1 living body (test portion)
2 photoacoustic matching material
3 light irradiation portion
4 mirror
5 light source
6 probe
7 electric signal processing circuit
8 signal processing device
9 display device
10 cyst material

The invention claimed is:
1. A phantom for a photoacoustic wave diagnostic apparatus, the phantom comprising:
a base material; and
an object to be detected,
wherein the base material and the object to be detected contain polyol, an inorganic oxide and a pigment which are dispersable in the polyol, and an isocyanate compound,
wherein a dispersed amount of the inorganic oxide to the polyol is in a range of 0.10 to 0.25 percent by weight,
wherein a dispersed amount of the pigment to the polyol is in a range of 0.0001 to 0.0005 percent by weight, and
wherein the dispersed amount of the pigment to the polyol in the base material is different from the dispersed amount of the pigment to the polyol in the object to be detected.
2. The phantom for the photoacoustic wave diagnostic apparatus according to claim 1, wherein the inorganic oxide includes titanium oxide.

3. The phantom for the photoacoustic wave diagnostic apparatus according to claim 1, wherein the pigment includes carbon black.

4. The phantom for the photoacoustic wave diagnostic apparatus according to claim 1, wherein the isocyanate compound includes hexamethylene diisocyanate.

* * * * *